United States Patent
Namba et al.

(10) Patent No.: US 11,939,290 B2
(45) Date of Patent: Mar. 26, 2024

(54) HETEROCYCLE-CONTAINING AMINO ACID COMPOUND AND SALT THEREOF, COMPLEX, COMPOSITION, FERTILIZER AND PLANT GROWTH REGULATOR

(71) Applicants: TOKUSHIMA UNIVERSITY, Tokushima (JP); AICHI STEEL CORPORATION, Tokai (JP)

(72) Inventors: Kosuke Namba, Tokushima (JP); Motofumi Suzuki, Tokai (JP); Akane Mera, Tokai (JP)

(73) Assignees: TOKUSHIMA UNIVERSITY, Tokushima (JP); AICHI STEEL CORPORATION, Tokai (JP)

( * ) Notice: Subject to any disclaimer, the term of this patent is extended or adjusted under 35 U.S.C. 154(b) by 624 days.

(21) Appl. No.: 17/270,334

(22) PCT Filed: Aug. 22, 2019

(86) PCT No.: PCT/JP2019/032904
§ 371 (c)(1),
(2) Date: Feb. 22, 2021

(87) PCT Pub. No.: WO2020/045247
PCT Pub. Date: Mar. 5, 2020

(65) Prior Publication Data
US 2021/0253522 A1 Aug. 19, 2021

(30) Foreign Application Priority Data
Aug. 29, 2018 (JP) .................................. 2018-160612

(51) Int. Cl.
| | | |
|---|---|---|
| *C07D 207/16* | (2006.01) | |
| *A01N 43/36* | (2006.01) | |
| *A01N 59/16* | (2006.01) | |
| *C05C 11/00* | (2006.01) | |
| *C07F 15/02* | (2006.01) | |

(52) U.S. Cl.
CPC ........... *C07D 207/16* (2013.01); *A01N 43/36* (2013.01); *A01N 59/16* (2013.01); *C05C 11/00* (2013.01); *C07F 15/02* (2013.01)

(58) Field of Classification Search
CPC .................................................... C12N 15/09
See application file for complete search history.

(56) References Cited

U.S. PATENT DOCUMENTS

| 10,638,758 B2 | 5/2020 | Namba et al. |
| 2010/0256395 A1 | 10/2010 | Namba et al. |

FOREIGN PATENT DOCUMENTS

| CN | 101195598 A | 6/2008 |
| JP | 54-128563 A | 10/1979 |
| JP | 2001-316192 A | 11/2001 |
| JP | 2017-60426 A | 3/2017 |
| JP | 2018-52865 A | 4/2018 |
| WO | WO 2017/082111 A1 | 5/2017 |

OTHER PUBLICATIONS

International Search Report dated Nov. 5, 2019 in PCT/JP2019/032904 filed on Aug. 22, 2019, 2 pages.
Scholz, G. et al., "Structure-Function Relationships of Nicotianamine Analogues," Phytochemistry, vol. 27, No. 9, 1988, pp. 2749-2754.
Anderegg, G. et al., "Correlation between Metal Complex Formation and Biological Activity of Nicotianamine Analogues," Journal of The Chemical Society, Chemical Communications, No. 10, 1989, pp. 647-650, 6 total pages.
Ripperger, H., "Deaminonicotianamine and 2-Decarboxynicotianamine," Journal fuer Praktische Chemie, vol. 328, No. 5-6, 1986, pp. 719-723.
Nishimaru, T. et al., "Study on the Structure Activity Relationship of a Phytosiderophore, Mugineic Acid," Peptide Science, Proceedings of the 42nd Japanese Peptide Symposium, 2005, pp. 263-266, 6 total pages.
Wakamiya, T. et al., "Study on the Relationship between Structure and Metal-Complexation Ability of Mugineic Acid," Peptide Science, Proceedings of the 35th Japanese Peptide Symposium, 1998, pp. 465-468, 6 total pages.
Watanabe, H., "A New Efficient Synthesis of Nicotianamine analogues and a Study on Structure-activity Relationships," Hasegawa Letter, No. 23, 2007, pp. 34-39, 8 total pages (with partial English translation).
Office Action dated Oct. 27, 2023, in corresponding European Patent Application No. 19 854 627.7, 4 pages.

(Continued)

*Primary Examiner* — Audrea B Coniglio
(74) *Attorney, Agent, or Firm* — Oblon, McClelland, Maier & Neustadt, L.L.P.

(57) ABSTRACT

The present invention is a heterocycle-containing amino acid compound represented by a general formula (1):

wherein $R^1$ and $R^2$ are identical with or different from each other, and each represent a hydrogen atom or a carboxy-protecting group;
$R^3$ represents a carboxyl group or a hydroxyl group; and
n is 1 or 2,
or a salt thereof.

12 Claims, 1 Drawing Sheet

(56) References Cited

OTHER PUBLICATIONS

Extended European Search Report dated Mar. 18, 2022 in European Patent Application No. 19854627.7, 5 pages.
Chinese Office Action dated Aug. 19, 2023 in Chinese Patent Application No. 201980056236.8 (with unedited computer-generated English translation), 8 pages.
Combined Chinese Office Action and Search Report dated Mar. 30, 2023 in Chinese Patent Application No. 201980056236.8 (with unedited computer-generated English translation of the Office Action), 11 pages.
Indian Office Action dated May 24, 2022, in Indian patent application No. 202147009188, 6 pages.

HETEROCYCLE-CONTAINING AMINO ACID COMPOUND AND SALT THEREOF, COMPLEX, COMPOSITION, FERTILIZER AND PLANT GROWTH REGULATOR

FIELD OF THE INVENTION

The present invention relates to a novel heterocycle-containing amino acid compound or a salt thereof, and to use thereof.

BACKGROUND ART

Various trace metal elements are involved in maintenance and function of plant growth. If the trace metal elements are deficient, the plant cannot grow normally. For example, iron is an element necessary for respiration, photosynthesis, DNA synthesis, etc., and is an active center metal of an enzyme particularly necessary for chlorophyll biosynthesis. Therefore, iron deficiency occurs chlorosis (iron-deficiency chlorosis) which causes yellowing of leaves.

On the other hand, a poor soil, which is considered unsuitable for agriculture, accounts for about 67% of the total land area in the world, and a half thereof is of an alkaline soil. In such alkaline soil, iron exists in a form of trivalent ferric hydroxide ($Fe(OH)_3$), which is insoluble in water. Plants cannot absorb iron sufficiently from the roots, so that iron deficiency disadvantageously occurs.

It is known that gramineous plants such as barley, rice, wheat, and corn secrete from the roots a substance capable of forming a chelate such as deoxymugineic acid (DMA) represented by the following formula (A); that the chelate-forming substance is complexed with iron, thereby dissolving iron; and that the complex of iron and a compound in mugineic acids is taken into the plant bodies via a specific transporter.

(A)

As a result, an iron ion can be absorbed from an alkaline soil. However, in strongly-alkaline soil, the amount of mugineic acids secreted is usually insufficient, and the growth of many gramineous plants is restricted.

In view of the above situation, the present inventors have aimed to develop a chelating agent with an iron uptake ability, which can be supplied as a fertilizer, in order to enable agriculture even in an alkaline soil. The present inventors have so far developed a heterocycle-containing amino acid compound or a salt thereof, which can be used as a fertilizer and a plant growth regulating agent, can exhibit an effect on the growth of plants such as gramineous plants even in an alkaline soil, and can be synthesized at a low cost (see, for example, Patent Literature 1).

PRIOR ART LITERATURE

[Patent Literature]

Patent Literature 1: WO2017/082111

SUMMARY OF THE INVENTION

[Problems that the Invention is to Solve]

The heterocycle-containing amino acid compound in the Patent Literature 1 is an analogue of mugineic acid, can be used as a fertilizer, a plant growth regulating agent, and the like, and, for example when applied to alkaline soil, allows plants to efficient absorb iron and can enhance the leaf color. Fertilizers, plant growth regulating agents and the like may be liquid in nature, and in this case, they would contain an acidic aqueous solution obtained by dissolving a heterocycle-containing amino acid compound or a salt thereof in water. When such liquid fertilizers, plant growth regulating agents, and the like are used, they may be stored for a long period of time. Therefore, excellent storage stability of an acidic aqueous solution is desired.

An object of the present invention is to provide a novel heterocycle-containing amino acid compound which has a metal uptake ability equal to or higher than that of a compound in mugineic acids, and has higher stability and is difficult to decompose in an acidic aqueous solution than that of a compound in mugineic acids. In addition, an object of the present invention is to provide a fertilizer or a plant growth regulating agent containing such a novel heterocycle-containing amino acid compound.

[Means for Solving the Problems]

The present inventors conducted earnest research in view of the above problems. As a result, the present inventors found a novel heterocycle-containing amino acid compound and a salt thereof having a metal uptake ability equal to or higher than that of a compound in mugineic acids and having higher stability than that of a compound in mugineic acids, in other words, being difficult to decompose during storage of an acidic aqueous solution prepared by dissolving it in water.

The present invention is as follows.

An invention described in claim 1 is a heterocycle-containing amino acid compound which is characterized in representing by a general formula (1);

(1)

(In the formula, $R^1$ and $R^2$ may be identical with or different from each other, and each represent a hydrogen atom or a carboxy-protecting group, $R^3$ represents a carboxyl group or a hydroxyl group, and n is 1 or 2.)

or a salt thereof.

An invention described in claim 2 is a heterocycle-containing amino acid compound or a salt thereof which is characterized in that the heterocycle-containing amino acid compound represented by the general formula (1) is a compound represented by a general formula (1A).

(1A)

(In the formula, $R^1$, $R^2$, $R^3$ and n are respectively the same as those above.)

An invention described in claim 3 is a heterocycle-containing amino acid compound or a salt thereof which is characterized in that the heterocycle-containing amino acid compound represented by the general formula (1) is a compound represented by a general formula (1B).

(1B)

(In the formula, $R^1$, $R^2$, $R^3$ and n are respectively the same as those above.)

An invention described in claim 4 is a heterocycle-containing amino acid compound or a salt thereof which is characterized in that $R^1$ and $R^2$ in the general formula (1), (1A) or (1B) are hydrogen atoms.

An invention described in claim 5 is a heterocycle-containing amino acid compound or a salt thereof which is characterized in that n in the general formula (1), (1A) or (1B) is 1 on basis of any one of claims 1 to 4.

An invention described in claim 6 is a complex which is characterized by including the heterocycle-containing amino acid compound or salt thereof according to any one of claims 1 to 5, and a metal.

An invention described in claim 7 is a complex which is characterized in that the metal is an iron.

An invention described in claim 8 is a composition which is characterized by including the heterocycle-containing amino acid compound or salt thereof according to any one of claims 1 to 5, and a metal compound.

An invention described in claim 9 is a composition which is characterized in that the metal compound is an iron compound.

An invention described in claim 10 is a composition which is characterized in that it is used for a fertilizer or a plant growth regulating agent on basis of any one of claim 8 or 9.

An invention described in claim 11 is a fertilizer which is characterized by including the heterocycle-containing amino acid compound or salt thereof according to any one of claims 1 to 5, the complex according to claim 6 or 7, or the composition according to any one of claims 8 to 10.

An invention described in claim 12 is a plant growth regulating agent which is characterized by including the heterocycle-containing amino acid compound or salt thereof according to any one of claims 1 to 5, the complex according to claim 6 or 7, or the composition according to any one of claims 8 to 10.

[Effects of the Invention]

According to one aspect of the present invention, the heterocycle-containing amino acid compound or salt thereof has a metal uptake ability equal to or higher than that of a compound in mugineic acids. An acidic aqueous solution is obtained by dissolving this compound in water, and is more stable than an acidic aqueous solution of a compound in mugineic acids. In other words, the heterocycle-containing amino acid compound or salt thereof of the present invention is difficult to decompose in water.

Further, the heterocycle-containing amino acid compound or salt thereof of the present invention can be suitably used as a raw material component for a fertilizer and a plant growth regulating agent. When a fertilizer or a plant growth regulating agent contains water, the heterocycle-containing amino acid compound or salt thereof of the present invention is highly stable in the aqueous solution during storage. Thus, even a fertilizer or the like stored for a long time more reliably functions on plants. It exerts a great effect on the growth of plants such as gramineous plants particularly in alkaline soil.

EMBODIMENT FOR CARRYING OUT THE INVENTION

The heterocycle-containing amino acid compound or salt thereof (hereinafter, referred to as "heterocycle-containing amino acid compound (1) or salt thereof") and use thereof of the present invention will be described in detail.

In the present specification, terms "containing" or "including" have concepts of "containing", "including", "consisting essentially of", or "consisting only of".

1. Heterocycle-Containing Amino Acid Compound (1) or Salt Thereof

In the general formula (1), $R^1$ and $R^2$ may be identical with or different from each other, and are each a hydrogen atom or a carboxyl-protecting group. The carboxyl-protecting group represented by $R^1$ and $R^2$ is not particularly limited, and example thereof includes a linear, a branched, or a cyclic alkyl group having 1 to 6 carbon atoms, such as methyl group, ethyl group, n-propyl group, iso-propyl group, n-butyl group, iso-butyl group, tert-butyl group, n-hexyl group, and cyclohexyl group; an aralkyl group which may have a substituent, such as benzyl group, p-nitrobenzyl group, o-nitrobenzyl group, m-nitrobenzyl group, 2,4-dinitrobenzyl group, p-chlorobenzyl group, p-bromobenzyl group, and p-methoxybenzyl group; an alkylcarbonyloxy-alkyl group, the alkylcarbonyloxy having 1 to 6 carbon atoms, such as acetoxymethyl group, acetoxyethyl group, propionyloxymethyl group, n-butyryloxymethyl group, iso-butyryloxymethyl group, and pivaloyloxymethyl group; and the like. Among the protective group, an alkyl group having 1 to 6 carbon atoms is preferable, ethyl group or tert-butyl group is more preferable, and ethyl group is particularly preferable.

In the specification, "n-" means normal; "iso-" means iso; "tert-" means tertiary; "o-" means ortho; "m-" means meta; and "p-" means para.

Further, in the general formula (1), $R^3$ is a carboxyl group or a hydroxyl group.

In the present invention, the heterocycle-containing amino acid compound (1) or salt thereof is preferably a compound in which $R^1$ and $R^2$ may be identical with or different from each other, and are each a hydrogen atom, or a linear alkyl group or branched alkyl group, having 1 to 6 carbon atoms, and $R^3$ is a carboxyl group or a hydroxyl group, or a salt thereof.

In the present invention, the heterocycle-containing amino acid compound (1) or salt thereof is more preferably a compound in which $R^1$ and $R^2$ may be identical with or different from each other, and are each a hydrogen atom, an ethyl group or a tert-butyl group, and $R^3$ is a carboxyl group or a hydroxyl group, or a salt thereof, further preferably a compound in which $R^1$ and $R^2$ may be identical with or different from each other, and are each a hydrogen atom or an ethyl group, and $R^3$ is a carboxyl group or a hydroxyl group, or a salt thereof, and is particularly a compound in which $R^1$ and $R^2$ are hydrogen atoms, and $R^3$ is a carboxyl group or a hydroxyl group, or a salt thereof.

For example, the heterocycle-containing amino acid compound (1) when $R^1$ and $R^2$ are each a hydrogen atom is represented by a following general formula (1C-1).

(1C-1)

(In the formula, n is 1 or 2.)

The heterocycle-containing amino acid compound (1) can also be represented by a following formula (1C-2).

(1C-2)

(In the formula, n is 1 or 2.)

In the heterocycle-containing amino acid compound (1) or salt thereof, n in the general formula (1) is 1 or 2. In the general formula (1), the heterocycle-containing amino acid compound (1) wherein n is 1 is a compound represented by a following formula (1-1), and the heterocycle-containing amino acid compound (1) wherein n is 2 is a compound represented by a following formula (1-2). The preferable compound is a compound wherein n is 1.

(1-1)

(1-2)

The heterocycle-containing amino acid compound (1) or salt thereof may have an isomer such as optical isomers, stereoisomers and position isomers. For example, when the heterocycle-containing amino acid compound (1) or salt thereof has optical isomers, optical isomers divided from a racemic body are also included in the compound (1) or a salt thereof.

Examples of optical isomers which are preferable as the heterocycle-containing amino acid compound (1) or salt thereof include compounds represented by following general formulae (1A) and (1B) or salts thereof.

(1A)

(In the formula, $R^1$, $R^2$, $R^3$ and n are as described above.)

(1B)

(In the formula, $R^1$, $R^2$, $R^3$ and n are as described above.)

The compounds represented by general formulae (1A) and (1B) or salts thereof are preferably compounds in which $R^1$ and $R^2$ are each a hydrogen atom and n is 1 or 2, or salts thereof, and particularly compounds in which $R^1$ and $R^2$ are each a hydrogen atom, $R^3$ is a hydroxyl group or a carboxyl group, and n is 1, or salts thereof.

The salt of the heterocycle-containing amino acid compound (1) is not particularly limited. Example of such salt includes an inorganic acid salt such as hydrochlorides, sulfates and nitrates; an organic acid salt such as acetates and methanesulfonates; an alkali metal salt such as sodium salts and potassium salts; an alkaline earth metal salt such as magnesium salts and calcium salts; a quaternary ammonium salt such as dimethylammonium and triethylammonium; and the like. These salts are suitable in the agricultural field.

2. Method for Producing Heterocycle-Containing Amino Acid Compound (1) or Salt Thereof The heterocycle-containing amino acid compound (1) or salt thereof can be produced, for example, by a method including sequentially step 1, step 2, step 3, step 4, and step 5 (hereinafter, this method is referred to as "first method"), or a method including sequentially step 1, step 2, step 3', and step 4' (hereinafter, this method is referred to as "second method"). Specifically, the first method leads to production of a heterocycle-containing amino acid compound of general formula (1) in which $R^3$ is a hydroxyl group, or a salt thereof.

(In the formula, $R^{10}$ and $R^{20}$ may be identical with or different from each other, and are each a carboxyl-protecting group; $R^{30}$ is a hydroxyl-protecting group; $R^{50}$ is an amino-protecting group; and n is 1 or 2.)

Note that $R^{10}$ and $R^{20}$, which are carboxy-protecting groups, have the same meanings as the respective protecting groups represented by $R^1$ and $R^2$ described above.

Further, the second method leads to production of a heterocycle-containing amino acid compound of general formula (1) in which $R^3$ is a carboxyl group, or a salt thereof.

(In the formula, $R^{10}$, $R^{20}$ and $R^{40}$ may be identical with or different from each other, and are each a carboxyl-protecting group.)

First, each of the steps in the first method will be described.

The step 1 is a step in which a compound represented by general formula (5) (hereinafter, referred to as "compound (5)") is subjected to oxidatively cleavage of a vinyl group in the compound to form an aldehyde, and then the aldehyde and a compound represented by general formula (6) (hereinafter, referred to as "compound (6)") are subjected to reaction (reductive amination) to yield a compound represented by general formula (4) (hereinafter, referred to as "compound (4)").

The compound (5) is a compound having —$CO_2R^{20}$ including a carboxyl-protecting group $R^{20}$ and —$NHR^{50}$ including an amino-protecting group $R^{50}$.

Examples of the amino-protecting group $R^{50}$ include an alkoxycarbonyl group which may be substituted with halogen, such as methoxycarbonyl group, ethoxycarbonyl group, 2,2,2-trichloroethoxycarbonyl group, and tert-butoxycarbonyl group (Boc); an alkenyloxycarbonyl group such as vinyloxycarbonyl group; an aralkyloxycarbonyl group such as benzyloxycarbonyl group (Cbz) and 9-fluorenylmethoxycarbonyl group; an aralkyl group which may have a substituent, such as benzyl group, p-nitrobenzyl group, o-nitrobenzyl group, m-nitrobenzyl group, 2,4-dinitrobenzyl group, p-chlorobenzyl group, p-bromobenzyl group, and p-methoxybenzyl group; an acyl group such as formyl group, acetyl group, trifluoroacetyl group, and benzoyl group; an arylsulfonyl group such as p-toluenesulfonyl group and benzenesulfonyl group; an alkylsulfonyl group such as methanesulfonyl group; and the like.

Among these, the amino-protecting group $R^{50}$ is preferably an alkoxycarbonyl group or aralkyloxycarbonyl group, and more preferably Boc or Cbz.

The compound (5) to be used is preferably an allylglycine in which a carboxyl group is protected with a protecting group $R^{20}$ and an amino group is protected with a protecting group $R^{50}$. Examples of particularly preferred compound (5) include Boc-L-allylglycine, Cbz-L-allylglycine, compounds in which carboxyl groups thereof are protected with a protecting group, and the like. A commercially available product can be used as the compound (5). When there is no commercially available product, Boc-L-allylglycine and Cbz-L-allylglycine can be produced from commercially available L-allylglycine, for example, according to the method described in PROTECTIVE GROUPS in ORGANIC SYNTHESIS (authored by T. W. Green; P. G.M. Wuts).

Examples of the compound (6) include proline, pipecolic acid, and the like.

The step 1 includes a process of oxidatively cleaving a vinyl group in the compound (5) to yield an aldehyde, and a process of subjecting the aldehyde and the compound (6) to a reductive amination. Proportions of the compound (5) and the compound (6) to be used are not particularly limited and can appropriately be selected from a wide range. The compound (6) is used in an amount of usually about 1 to 5 mol, and preferably about 1 to 2 mol based on 1 mol of the compound (5).

The oxidative cleavage reaction is carried out in the presence of an oxidant. Examples of the oxidant include ozone ($O_3$), permanganates, $RuCl_3$, $OsO_4$—$NaIO_4$, and the like. Among these, ozone is preferable. Amount to be used of the oxidant is not particularly limited. When ozone is used as the oxidant, a gas generated by an ozone gas generator or the like, for example, can be used.

The oxidative cleavage reaction using ozone can be carried out by, for example, blowing ozone gas into a solution in which the compound (5) is dissolved in a solvent (bubbling). Examples of the solvent include an alcohol-based solvent such as methanol and ethanol; a chlorine-based solvent such as dichloromethane and chloroform; ethyl acetate and the like. The solvent is preferably methanol.

The reaction temperature and reaction time in the oxidative cleavage process are not particularly limited. When ozone gas is used as the oxidant and is bubbled, the reaction temperature is preferably set to a low temperature ranging from about −100° C. to −50° C. The bubbling of ozone gas is preferably performed until the solution turns blue since the solution is colored blue when oxidative cleavage by ozone is completed and ozone is saturated in the solution.

After the bubbling of the ozone gas, it is preferable to bubble, for example, oxygen, nitrogen, or argon gas in the solution until the blue color of the solution disappears in order to remove excess ozone. Thus, an aldehyde can be obtained.

Subsequently, the reductive amination between the aldehyde and the compound (6) is carried out in the presence of a reducing agent. Following the oxidative cleavage reaction, the reductive amination can be carried out in one pot. Alternatively, it can be carried out in other reaction system after the obtainment of the aldehyde by the oxidative cleavage reaction. Examples of the reducing agent include a boron compound such as sodium cyanoborohydride and sodium triacetoxyborohydride. Among these, sodium triacetoxyborohydride (NaBH(OAc)$_3$) is preferred.

An amount of the reducing agent to be used is not particularly limited and may appropriately be selected from a wide range. The reducing agent is used in an amount of usually about 1 to 5 mol, and preferably about 1 to 2 mol based on 1 mol of the compound (5). A pH in the reductive amination is usually about 4 to 7, and preferably about 6 to 7. The reaction temperature and reaction time in the reductive amination are not particularly limited. The reductive amination can be carried out under any of cooling, room temperature and heating. The reaction time may be set to 30 minutes to 24 hours under a temperature condition of, for example about 25° C. to 50° C.

When the reaction mixture obtained in the step 1 is subjected to isolation such as filtration, concentration and extraction after cooling of the reaction mixture to separate a coarse reaction product, and then the coarse reaction product is subjected to an ordinary purification such as column chromatography, contact to ion exchange resin and recrystallization, the compound (4) can be isolated and purified. The reaction mixture can also be used in the subsequent step 2 without isolation or purification of the compound (4).

The step 2 is a step in which the compound (4) is subjected to protection for protecting a carboxyl group in the compound (4) with the protecting group $R^{10}$ and to deprotection for deprotecting the amino-protecting group $R^{50}$ to yield a compound represented by general formula (3) (hereinafter, referred to as "compound (3)") or a salt thereof.

A reaction for protecting the carboxyl group in the compound (4) with the protecting group $R^{10}$ is not particularly limited, and a known method can be used. The above scheme is a method using an alcohol $R^{10}OH$, and includes a dehydration condensation reaction between the compound (4) and the alcohol $R^{10}OH$. Examples of the alcohol used in this reaction include methanol, ethanol, tert-butanol, and the like.

The reaction for deprotecting the amino-protecting group $R^{50}$ is not particularly limited. For example, (i) a deprotection method using an acid or a base, (ii) a deprotection method through catalytic reduction, or the like may be applied according to the known method described in the document (see Protective Groups in Organic Synthesis, T. W. Greene, John Wiley & Sons (1981)) or a method equivalent thereto.

Examples of the acid used in the deprotecting reaction (i) include an inorganic acid such as hydrogen chloride (or hydrochloric acid), hydrogen bromide (or hydrobromic acid), hydrogen fluoride (or hydrofluoric acid), hydrogen iodide (or hydriodic acid), aluminum chloride, aluminum bromide, boron trichloride, boron tribromide, sulfuric acid, and phosphoric acid; an organic acid such as formic acid, acetic acid, trifluoroacetic acid, propionic acid, methanesulfonic acid, p-toluenesulfonic acid, and trifluoromethanesulfonic acid; and the like. An acidic ion exchange resin may also be used.

Examples of the base used in the deprotecting reaction (i) include an inorganic base such as sodium hydroxide, potassium hydroxide, calcium hydroxide and magnesium hydroxide; and an organic base such as a metal alkoxide, an organic amine, and a quaternary ammonium salt. A basic ion exchange resin may also be used.

An amount of the acid or base to be used is not particularly limited and is usually 1 to 50 mol, and preferably 1 to 30 mol based on 1 mol of the compound (4).

The deprotecting reaction (i) using an acid or a base can be carried out in a solvent-free manner or in a solvent. In a case where solvent is used, the solvent is not particularly limited so long as it does not adversely affect the reaction. Examples of the solvent include an alcohol-based solvent such as methanol and ethanol; an aprotic polar solvent such as acetonitrile, dimethylformamide (DMF), and dimethylsulfoxide (DMSO); a halogenated hydrocarbon-based solvent such as methylene chloride (DCM) and 1,2-dichloroethane (DCE); and the like. These solvents may be used singly or in combination of two or more types thereof.

A specific example of the step 2 including the deprotecting reaction (i) is described. In a case where $R^{50}$ in the compound (4) is a Boc group or the like, when the compound (4) and a hydrochloric acid/ethanol solution are reacted, a reaction for protecting the carboxyl group with an ethyl group which is the protecting group $R^{10}$ and the deprotecting reaction (i) of the amino-protecting group $R_{50}$ can be simultaneously carried out. The hydrochloric acid/ethanol solution can be prepared, for example, by a method of adding acetyl chloride (AcCl) to an excessive amount of ethanol or a method of bubbling hydrochloric acid gas into ethanol. Proportions of acetyl chloride and ethanol are not particularly limited. A proportion of ethanol can be set to about 20 to 50 times volume relative to 1 volume of acetyl chloride.

In the method of bubbling hydrochloric acid gas into ethanol, an amount of dissolved hydrochloric acid can be set by comparing the previously measured weight of ethanol with the weight of ethanol after bubbling of hydrochloric acid gas. After completion of the reaction in the step 2, the reaction mixture is, for example, concentrated under a reduced pressure; toluene or the like is added thereto; and then the solvent can be distilled away by azeotropic distillation. Furthermore, after the azeotropic distillation, the reaction mixture can be dried by suction with a vacuum pump or the like.

The reaction temperature and reaction time of the deprotection reaction (i) are not particularly limited. The deprotection reaction (i) can be carried out under any of cooling, room temperature and heating. The preferable reaction time is approximately in a range from 1 to 30 hours under a temperature condition of, for example, about 0° C. to 100° C.

The deprotection method (ii) through catalytic reduction can be applied, for example, in a case where $R^{50}$ in the compound (4) is a group to be hydrocracked. Examples of the deprotecting reaction (ii) include a method in which hydrocracking with a transition metal catalyst such as Pd, Pt, Ru, and Rh is used; a method in which hydrocracking with a catalyst having carried thereon a transition metal such as Pd-carbon and palladium hydroxide-carbon (Pearlman's catalyst) is used; a Birch reduction method; and the like. Among these methods, a method using Pd-carbon is preferable. Furthermore, the transition metal catalyst is used in an amount of usually 0.01 to 5 mol, and preferably about 0.05 to 0.2 mol based on 1 mol of the compound (4).

The reaction temperature and reaction time in the deprotection reaction (ii) through catalytic reduction are not particularly limited. The deprotection reaction (i) can be carried out under any of cooling, room temperature and heating. The reaction time is preferably in a range from 1 to 24 hours under a temperature condition of about 10° C. to 40° C. Further, the pressure in the deprotection reaction (ii) through catalytic reduction is not particularly limited, but the reaction is usually carried out in hydrogen atmosphere of 1 to 4 atoms. The preferable reaction pressure is 1 to 2 atoms.

The deprotecting reaction (ii) through catalytic reduction is usually carried out in a solvent. The solvent is not particularly limited so long as it does not adversely affect the reaction. Examples of the solvent include an alcohol-based solvent such as methanol and ethanol; an ether-based solvent such as tetrahydrofuran (THF), methyl-tert-butylether (MTBE), dioxane, diethylether, dimethoxyethane, and diglyme; an ester-based solvent such as methyl acetate and ethyl acetate; a halogenated hydrocarbon-based solvent such as DCM and DCE; water; and the like. These solvents may be used singly or in combination of two or more types thereof. The solvent is preferably an alcohol-based solvent such as methanol and ethanol.

When the reaction mixture obtained in the step 2 is subjected to isolation such as filtration, concentration and extraction after cooling of the reaction mixture to separate a coarse reaction product, and then the coarse reaction product is subjected to an ordinary purification such as column chromatography, contact to ion exchange resin and recrystallization, the compound (3) can be isolated and purified. The reaction mixture can also be used in the subsequent step 3 without isolation or purification of the compound (3).

While the compound (3) obtained by the step 2 has a free amino group, this amino group can be converted into a salt of an acid such as hydrochloric acid and sulfuric acid using a known method.

The step 3 is a step in which the compound (3) and an aldehyde compound represented by a general formula (2) (hereinafter, referred to as "aldehyde compound (2)") are subjected to reductive amination to yield a compound represented by a general formula (1') (hereinafter, referred to as "compound (1')").

The aldehyde compound (2) is a compound having —$OR^{30}$ including a hydroxyl-protecting group $R^{30}$ on one end side.

Examples of the hydroxyl-protecting group $R^{30}$ include a linear or branched alkyl group having 1 to 6 carbon atoms such as methyl group, ethyl group, n-propyl group, iso-propyl group, n-butyl group, iso-butyl group, tert-butyl group and n-hexyl group; an aralkyl group which may have 1 to 5 substituents, such as benzyl group, p-nitrobenzyl group, o-nitrobenzyl group, m-nitrobenzyl group, 2,4-dinitrobenzyl group, p-chlorobenzyl group, p-bromobenzyl group, and p-methoxybenzyl group; a trialkylsilyl group such as trimethylsilyl group, triethylsilyl group, and tert-butyldimethylsilyl group; an acetal type protecting group such as tetrahydropyran-2-yl group, methoxymethyl group, and methoxyethoxymethyl group; an alkoxycarbonyl group such as tert-butoxycarbonyl group; and the like.

Among these groups, the hydroxyl-protecting group $R^{30}$ is preferably an alkyl group having 1 to 6 carbon atoms or a trialkylsilyl group, more preferably ethyl group, tert-butyl group and tert-butyldimethylsilyl group (TBS), and particularly preferably TBS.

Examples of the aldehyde compound (2) include 3-hydroxypropionaldehyde which is protected with tert-butyldimethylsilyl group (TBS), and the like. The aldehyde compound (2) to be used may be one that is produced, for example, according to the method described in Nishimaru, T, et al. Peptide Science 2006, 42, 263-266, or a method equivalent thereto. The compound (2) is used in an amount of usually at least 1 mol, and preferably about 1 to 5 mol based on 1 mol of the compound (3) in the step 3.

The reaction in the step 3 can be carried out in a solvent in the presence of a reducing agent. A compound capable of using for the reductive amination in the step 1 may be used as the reducing agent. The reducing agent is preferably a sodium cyanoborohydride ($NaBH_3CN$). The reducing agent is used in an amount of usually 0.5 to 10 mol, and preferably about 1 to 6 mol based on 1 mol of the compound (3).

The solvent is not particularly limited so long as it does not adversely affect the reaction. Examples of the solvent include an alcohol-based solvent such as methanol, ethanol, isopropyl alcohol, and ethylene glycol; an aprotic polar solvent such as acetonitrile, DMF, and DMSO; and the like. These solvents may be used singly or in combination of two or more types thereof.

The reaction temperature and reaction time of the reductive amination are not particularly limited. The reductive amination can be carried out under any of cooling, room temperature and heating. The preferable reaction time is approximately in a range from 1 to 30 hours under a temperature condition of about 0° C. to 100° C.

Further, the secondary amino group in the compound obtained by the reductive amination may be protected with an amino-protecting group using a known method, as necessary. Examples of the amino-protecting group include the functional groups exemplified as $R^{50}$ above.

When the reaction mixture obtained in the step 3 is subjected to isolation such as filtration, concentration and extraction after cooling of the reaction mixture to separate a coarse reaction product, and then the coarse reaction product is subjected to an ordinary purification such as column chromatography, contact to ion exchange resin and recrystallization, the compound (1') can be isolated and purified. The reaction mixture can also be used in the subsequent step 4 without isolation or purification of the compound (1').

The step 4 is a step in which the compound (1') is subjected to deprotection for deprotecting the hydroxyl-protecting group $R^{30}$ in the compound (1') to yield a compound represented by a general formula (1") (hereinafter, referred to as "compound (1")"). The compound (1") is included in the heterocycle-containing amino acid compound (1) of the present invention.

Examples of the deprotection method in the step 4 include a deprotection method using an acid or a base, a deprotection method through catalytic reduction, a combination thereof, and the like. In these deprotection methods, publicly known methods may be applied such as the deprotection methods (i) and (ii) in the step 2. For example, when the protecting group $R^{30}$ is a protecting group which can be deprotected with an acid, a deprotection method using an acid can be applied. Further, when the protecting group $R^{30}$ is a protecting group which can be deprotected with a base, a deprotection method using a base can be applied.

The deprotecting method using an acid or a base can be carried out in a solvent. Examples of the solvent include water; an alcohol-based solvent such as methanol, ethanol and tert-butanol; a halogenated hydrocarbon-based solvent such as DCM, chloroform, and DCE; an ether-based solvent such as THF, MTBE, dioxane, diethylether, dimethoxyethane, and diglyme; ethyl acetate; a ketone-based solvent such as acetone and methylethylketone; acetic acid; and the like. These solvents may be used singly or in combination of two or more types thereof.

A specific example of the step 4 is described. When the protecting group $R^{30}$ in the compound (1') is a tert-butyldimethylsilyl group, it is preferable to conduct deprotection with an acid. Examples of the acid include acetic acid, trifluoroacetic acid, and the like. The solvent is preferably a mixed solvent of THF and water.

In the deprotecting method using an acid or a base, an amount of the acid or base to be used is not particularly limited. An amount of the acid or base to be used is usually 1 to 20 mol, and preferably 1 to 10 mol based on 1 mol of the compound (1'). Furthermore, in the deprotection method using an acid or a base, when the acid or base itself is of a liquid, it can also serve as a solvent. Therefore, the acid or base can be used in excess.

The reaction temperature and reaction time in the deprotection method are not particularly limited. The deprotection method can be carried out under any of cooling, room temperature and heating. The reaction time is preferably in a range from 30 minutes to 30 hours under a temperature condition of about 0° C. to 85° C.

When the reaction mixture obtained in the step 4 is subjected to isolation such as filtration, concentration and extraction after cooling of the reaction mixture to separate a coarse reaction product, and then the coarse reaction product is subjected to an ordinary purification such as column chromatography, contact to ion exchange resin and recrystallization, the compound (1") can be isolated and purified. Further, these procedures lead to isolation of isomers.

The step 5 is a step in which the compound (1") is subjected to deprotection for deprotecting the carboxy-protecting groups $R^{10}$ and $R^{20}$ in the compound (1") to yield a compound represented by a general formula (1"-2) (hereinafter, referred to as "compound (1"-2)"). The compound (1"-2) is included in the salt of the heterocycle-containing amino acid compound (1) of the present invention.

Examples of the deprotection method in the step 5 include a deprotection method using an acid or a base, a deprotection method through catalytic reduction, a combination thereof, and the like. In these deprotection methods, publicly known methods may be applied such as the deprotection methods (i) and (ii) in the step 2. For example, when the protecting group $R^{10}$ and $R^{20}$ are protecting groups which can be deprotected with an acid, a deprotection method using an acid can be applied. Further, when the protecting group $R^{10}$ and $R^{20}$ are protecting groups which can be deprotected with a base, a deprotection method using a base can be applied.

The deprotecting method using an acid or a base can be carried out in a solvent. Examples of the solvent include water; an alcohol-based solvent such as methanol, ethanol and tert-butanol; a halogenated hydrocarbon-based solvent such as DCM, chloroform, and DCE; an ether-based solvent such as THF, MTBE, dioxane, diethylether, dimethoxyethane, and diglyme; ethyl acetate; a ketone-based solvent such as acetone and methylethylketone; acetic acid; and the like. These solvents may be used singly or in combination of two or more types thereof.

A specific example of the step 5 is described. When the protecting group $R^{10}$ and $R^{20}$ in the compound (1") are ethyl groups, it is preferably to conduct deprotection with a base. This time, sodium hydroxide is more preferably used as the base.

In the deprotecting method using an acid or a base, an amount of the acid or base to be used is not particularly limited. An amount of the acid or base to be used is usually 1 to 20 mol, and preferably 1 to 10 mol based on 1 mol of the compound (1"). Furthermore, in the deprotection method using an acid or a base, when the acid or base itself is of a liquid, it can also serve as a solvent. Therefore, the acid or base can be used in excess.

The reaction temperature and reaction time in the deprotection method are not particularly limited. The deprotection method can be carried out under any of cooling, room temperature and heating. The reaction time is preferably in a range from 30 minutes to 30 hours under a temperature condition of about 0° C. to 85° C.

When the reaction mixture obtained in the step 5 is subjected to isolation such as filtration, concentration and extraction after cooling of the reaction mixture to separate a coarse reaction product, and then the coarse reaction product is subjected to an ordinary purification such as column chromatography, contact to ion exchange resin and recrystallization, the compound (1"-2) can be isolated and purified.

Next, the step 3' and step 4' in the second method for producing a heterocycle-containing amino acid compound (1) in which $R^3$ is a carboxyl group in the general formula (1), or a salt thereof are described.

The step 3' is a step in which a reductive amination between the compound (3) that is a reaction product in the step 2 and an aldehyde compound represented by a general formula (2') (hereinafter, referred to as "aldehyde compound (2')") is conducted to yield a compound represented by a general formula (1''') (hereinafter, referred to as "compound (1''')"). The compound (1''') is included in the heterocycle-containing amino acid compound (1) of the present invention.

The aldehyde compound (2') is a compound having —$CO_2R^{40}$ including a carboxyl-protecting group $R^{40}$.

The carboxyl-protecting group $R^{40}$ is preferably a tert-butyldimethylsilyl (TBS) group.

Examples of the aldehyde compound (2') include succinic acid semialdehyde protected with a tert-butyldimethylsilyl group (TBS), and the like.

The aldehyde compound (2') is used in an amount of usually at least 1 mol, and preferably about 1 to 5 mol based on 1 mol of the compound (3).

The reaction in the step 3' can be carried out in a solvent in the presence of a reducing agent. A compound capable of using for the reductive amination in the step 1 may be used as the reducing agent. The reducing agent is used in an amount of usually 0.5 to 10 mol, and preferably 1 to 6 mol based on 1 mol of the compound (3).

The solvent is not particularly limited so long as it does not adversely affect the reaction. Examples of the solvent include an alcohol-based solvent such as methanol, ethanol, isopropyl alcohol, and ethylene glycol; an aprotic polar solvent such as acetonitrile, DMF, and DMSO; and the like. These solvents may be used singly or in combination of two or more types thereof.

The reaction temperature and reaction time of the reductive amination are not particularly limited. The reductive amination can be carried out under any of cooling, room temperature and heating. The preferable reaction time is approximately in a range from 1 to 30 hours under a temperature condition of about 0° C. to 100° C.

Further, the secondary amino group in the compound obtained by the reductive amination may be protected with an amino-protecting group using a known method, as necessary. Examples of the amino-protecting group include the functional groups exemplified as $R^{50}$ above.

When the reaction mixture obtained in the step 3' is subjected to isolation such as filtration, concentration and extraction after cooling of the reaction mixture to separate a coarse reaction product, and then the coarse reaction product is subjected to an ordinary purification such as column chromatography, contact to ion exchange resin and recrystallization, the compound (1''') can be isolated and purified. The reaction mixture can also be used in the subsequent step 4' without isolation or purification of the compound (1''').

The step 4' is a step in which the compound (1''') is subjected to deprotection for deprotecting the carboxy-protecting groups $R^{10}$, $R^{20}$ and $R^{40}$ in the compound (1''') to yield a compound represented by a general formula (1'''-2) (hereinafter, referred to as "compound (1'''-2)"). The compound (1'''-2) is included in the salt of the heterocycle-containing amino acid compound (1) of the present invention.

The aforementioned deprotection methods similar to those employed in the step 5 can be applied to this step 4' in that the carboxyl-protecting group is deprotected, and therefore the description thereof is omitted.

According to the step 4', the three carboxy-protecting groups in the compound (1''') can be deprotected in one step. Therefore, the number of steps required is smaller than that required in a case where a hydroxyl-protecting group is included.

3. Complex Including Heterocycle-Containing Amino Acid Compound (1) or Salt Thereof and Metal The heterocycle-containing amino acid compound (1) or salt thereof leads to a complex including a metal element. A complex including the heterocycle-containing amino acid compound (1) or salt thereof and a metal can be produced, for example, by dissolving the heterocycle-containing amino acid compound (1) or salt thereof and a metal compound which will be described below in a suitable solvent such as water and a buffer solution.

The metal element is not particularly limited, but examples of the metal element include a large-amount element such as magnesium (Mg) and calcium (Ca); a trace element such as iron (Fe), manganese (Mn), zinc (Zn), molybdenum (Mo), and copper (Cu); and the like. Among these metal elements, the metal element is preferably iron or copper, and more preferably iron, since it is a metal which is required, especially, in the plant body. These metal elements usually exist in a state of a metal ion (monovalent, divalent, and trivalent metal ions) in the complex, but may exist in a state of zero-valent metal. Only one metal element or two or more metal elements may be contained in the complex of the present invention.

In the complex of the present invention, a content of the metal element is not particularly limited, and may be an appropriate content depending on the purpose. The content of this metal element is usually in a range from 0.1% to 100% by mol, and preferably from 50% to 100% by mol relative to the heterocycle-containing amino acid compound (1) or salt thereof.

4. Composition Including Heterocycle-Containing Amino Acid Compound (1) or Salt Thereof and Metal Compound The composition of the present invention includes the heterocycle-containing amino acid compound (1) or salt thereof and a metal compound. This composition can be produced, for example, by mixing the heterocycle-containing amino acid compound (1) or salt thereof with the metal compound.

The metal compound is not particularly limited, but a compound having a metal element required in the plant body can be used. Specific examples of the compound include a magnesium compound, a calcium compound, an iron compound, a manganese compound, a boron compound, a zinc compound, a molybdenum compound, a copper compound, and the like.

Examples of the magnesium compound include magnesium hydroxide, magnesium chloride, and the like. Examples of the calcium compound include calcium hydroxide, calcium carbonate, calcium chloride, and the like. Examples of the iron compound include iron sulfate, iron nitrate, iron oxide ($Fe_2O_3$), ferric chloride ($FeCl_3$), and hydrates thereof, and the like.

Examples of the manganese compound include manganese dioxide, manganese sulfate pentahydrate, manganese chloride tetrahydrate, and the like. Examples of the boron compound include sodium tetraborate decahydrate, boric acid, and the like. Examples of the zinc compound include zinc sulfate, zinc oxide, and the like. Examples of the molybdenum compound include sodium molybdate, ammonium molybdate, and the like. Examples of the copper compound include copper sulfate, copper nitrate, and the like.

The metal compound in the composition of the present invention may be contained singly or in combination of two or more types thereof. In the present invention, the metal compound is preferably an iron compound or copper compound, and more preferably an iron compound. Iron sulfate and ferric chloride (hexahydrate) are particularly preferred. Further, a content of the metal compound is not particularly limited, but may be an appropriate content depending on the purpose. The content of the metal compound is preferably in a range from 0.1% to 100% by mol, and more preferably from 50% to 100% by mol relative to the heterocycle-containing amino acid compound (1) and salt thereof.

The composition of the present invention may further contain other components such as water, an organic solvent and a dispersant depending on the intended use.

When the composition of the present invention is composed only of solid components, the composition is solid in nature. When the composition of the present invention contains a liquid component, the composition is usually liquid in nature while it depends on the content proportion.

In the present invention, the heterocycle-containing amino acid compound (1) or salt thereof or the complex may be used to prepare other compositions suitable in the agricultural field. Other compositions as follows.

(a) A composition including two or more types of the heterocycle-containing amino acid compounds (1)
(b) A composition including two or more types of a salt of the heterocycle-containing amino acid compounds (1)
(c) A composition including two or more of the complexes
(d) A composition including the heterocycle-containing amino acid compound (1) and salt thereof (e) A composition including the heterocycle-containing amino acid compound (1) and the complex (f) A composition including a salt of the heterocycle-containing amino acid compound (1) and the complex (g) A composition including the heterocycle-containing amino acid compound (1) and salt thereof, and the complex (h) A composition including the complex and other compound (such as a metal compound)

5. Uses of Heterocycle-Containing Amino Acid Compound (1) or Salt Thereof, Complex, and Composition The heterocycle-containing amino acid compound (1) or salt thereof, complex, and composition can be used as a fertilizer, a plant growth regulating agent, and the like. Here, the term "plant growth regulating agent" means a plant growth promoter or a plant growth suppressor (plant growth inhibitor). In addition, the term "plant growth regulating agent" also includes the meaning of hormones.

The heterocycle-containing amino acid compound (1) or salt thereof in the fertilizer or plant growth regulating agent of the present invention may be contained singly or in combination of two or more types thereof. Furthermore, the fertilizer or plant growth regulating agent of the present invention may also include an active ingredient contained in publicly known fertilizers, plant growth regulating agents, or the like, a plant hormone, and the like, in addition to the heterocycle-containing amino acid compound (1) or salt thereof, complex, and composition. The heterocycle-containing amino acid compound (1) or salt thereof contained in the fertilizer or plant growth regulating agent of the present invention is preferably a compound in which $R^1$ and $R^2$ in the general formula (1) are hydrogen atoms, or a salt thereof. Further, when $R^1$ and $R^2$ are carboxy-protecting groups, they are preferably ethyl groups.

Crops to which the fertilizer or plant growth regulating agent may be applied include all of conventionally cultivated agricultural and horticultural plants. Specific examples of the plants include a gramineous plant such as rice, wheat and corn; a vegetable; a fruit tree; a flower, an ornamental plant, and the like.

EXAMPLES

Hereinafter, a heterocycle-containing amino acid compound or a salt thereof, and a method for producing the same are specifically described by way of Examples. The present invention is not limited to the Examples.

The following abbreviations may be used.
Ac: acetyl group
Et: ethyl group
Bu: butyl group
MeOH: methanol
EtOH: ethanol
TLC: thin layer chromatography
Boc: tert-butoxycarbonyl group
TBS: tert-butyldimethylsilyl group
M: molar concentration (mol/L)

Reaction products obtained by organic reactions were subjected to $^1$H NMR measurement using NMR apparatus "AV500" (model name) manufactured by Bruker. Chemical shifts were determined using heavy water as an internal standard. Division patterns are as follows:
s: singlet, d: doublet, t: triplet, q: quartet, m: multiplet, b: broad.

Example 1

Indicated are a production example of a compound (1"a) in which $R^1$ and $R^2$ are ethyl groups, $R^3$ is a hydroxyl group, and n is 1 in the general formula (1), and a production example of a compound (1"a-2) which is a salt of a compound in which $R^1$ and $R^2$ are hydrogen atoms, $R^3$ is a hydroxyl group, and n is 1 in the general formula (1) (hereinafter, referred to also as "derivative (X)").

(1) Step 1

A methanol solution of 2.6 g (9.58 mmol) of Boc-L-allylglycine (5a) was cooled to −78° C., and ozone gas was used and bubbled until the solution turned blue. Then, nitrogen gas was bubbled until the blue color disappeared, and 2.21 mg (19.2 mmol) of L-proline (6a) and 4.07 g (19.2 mmol) of sodium triacetoxyborohydride (NaBH(OAc)$_3$) were added to this solution. The materials were stirred at room temperature (25° C.) for 6 hours to conduct a reaction. The completion of the reaction was confirmed by TLC, and the reaction solution was concentrated under a reduced pressure. Subsequently, the obtained residue was dissolved in a 1M aqueous sodium hydroxide solution and washed with diethyl ether. A chloroform/methanol solvent mixture (CHCl$_3$:MeOH=9:1) was added to the collected aqueous layer, and the mixture was cooled to 0° C. Then, a 1M aqueous potassium hydrogen sulfate solution was added thereto, a chloroform/methanol solvent mixture ($CHCl_3$:MeOH=9:1) was added to this mixed solution for extraction, and the collected organic layer was dried over magnesium sulfate. After that, filtration was performed, and the filtrate was concentrated under a reduced pressure to yield 3.47 g of a colorless oily compound (4a).

(2) Step 2

To 3.47 g (9.34 mmol) of the compound (4a), cooled anhydrous HCl/EtOH (HCl/EtOH prepared using 8 mL of acetyl chloride and 40 mL of ethanol) was added, and the materials were stirred at 50° C. for 16 hours to deprotect an amino-protecting group while protecting a carboxyl group. The completion of the reaction was confirmed by TLC, and the reaction solution was concentrated under a reduced pressure. Subsequently, the obtained residue was washed with diethyl ether, and a 0.1M aqueous sodium hydroxide solution was added to the collected aqueous layer. Dichloromethane was added to this mixed solution for extraction, and the collected organic layer was dried over magnesium sulfate. After that, filtration was performed, and the filtrate was concentrated under a reduced pressure to yield 1.85 g of a colorless oily compound (3a).

(3) Step 3

To 17 mL of a methanol solution of 464.4 mg (1.7 mmol) of the compound (3a), 386 mg (2.05 mmol) of an aldehyde compound (2a) was added, and the materials were cooled to 0° C. To this mixed solution, 4.9 mL (85.6 mmol) of acetic acid and 1.18 mg (1.88 mmol) of $NaBH_3CN$ were added. The mixture was stored at 0° C. for 2 hours to react the compound (3a) with the aldehyde compound (2a). Subsequently, the completion of the reaction was confirmed by TLC, and a saturated aqueous sodium hydrogen carbonate solution was added to this reaction solution. Dichloromethane was added to this mixed solution for extraction, and the collected organic layer was dried over magnesium sulfate. After that, filtration was performed and the filtrate was concentrated under a reduced pressure. The obtained residue was purified by flash column chromatography to yield 382 mg (0.86 mmol, 51%) of a colorless oily compound (1'a). The developing solvent for flash column chromatography is n-hexane:ethyl acetate=2:1 to 1:1.

Compound (1'a)

$^1$H NMR (400 MHz, $CD_3OD$): δ 4.16 (q, J=7.0 Hz, 2H), 4.15 (q, J=7.0 Hz, 2H), 3.69 (t, J=5.7 Hz, 2H), 3.31-3.30 (m, 1H), 3.20-3.08 (m, 2H), 2.77 (ddd, J=15.4, 11.6, 9.1 Hz, 1H), 2.64 (dt, J=11.3, 7.0 Hz, 1H), 2.54 (dt, J=11.3, 7.0 Hz, 1H), 2.45 (ddd, J=12.3, 8.3, 4.8 Hz, 1H), 2.35 (qd, J=8.3, 2.3 Hz, 1H), 2.11 (m, 1H), 1.91-1.73 (m, 5H), 1.69 (quintet, J=6.8 Hz, 2H), 1.26 (t, J=7.0 Hz, 3H), 1.25 (t, J=7.0 Hz, 3H), 0.89 (s, 9H), 0.05 (s, 6H).

(4) Step 4

To 382 mg (0.86 mmol) of the compound (1'a), 2.4 mL of acetic acid, 0.8 mL of THF and 0.8 mL of water were added, and the materials were stirred at room temperature (25° C.) for 16 hours to conduct a deprotecting reaction. The completion of the reaction was confirmed by TLC, and the reaction solution was concentrated under a reduced pressure. Subsequently, the obtained residue was dissolved in ethyl acetate, and a saturated aqueous sodium hydrogen carbonate solution was added. Dichloromethane was then added to this mixed solution for extraction, and the collected organic layer was dried over magnesium sulfate. After that, filtration was performed and the filtrate was concentrated under a reduced pressure. The obtained residue was purified by flash column chromatography to yield 147.1 mg (0.45 mmol, 52%) of a colorless oily compound (1"a). The developing solvent for flash column chromatography is ethyl acetate:methanol=100:1 to 0:100.

Compound (1"a)

$^1$H NMR (400 MHz, $CD_3OD$): δ 4.17 (q, J=7.3 Hz, 2H), 4.16 (q, J=7.3 Hz, 2H), 3.34 (m, 1H), 3.21-3.09 (m, 2H), 2.80 (m, 1H), 2.68 (dt, J=11.6, 7.0 Hz, 1H), 2.56 (dt, J=11.3, 6.8 Hz, 1H), 2.45 (ddd, J=13.3, 8.8, 4.8 Hz, 1H), 2.34 (qd, J=8.3, 2.5 Hz, 1H), 2.10 (m, 1H), 1.92-1.74 (m, 5H), 1.70 (quintet, J=6.5 Hz, 2H), 1.26 (t, J=7.3 Hz, 3H), 1.25 (t, J=7.3 Hz, 3H).

(5) Step 5

147.1 mg (0.45 mmol) of the compound (1"a) was dissolved with water, and 4.4 mL of the aqueous solution was cooled to 0° C. Subsequently, 0.97 mL of a 1M aqueous sodium hydroxide solution was added to this aqueous solution. The temperature was raised to room temperature (25° C.), and the mixture was stirred for 17 hours to conduct a deprotecting reaction. The completion of the reaction was confirmed by TLC, and the reaction solution was concentrated under a reduced pressure. To the obtained residue, 4.4 mL of a 1M aqueous hydrogen chloride solution was added, and the mixture was stirred at room temperature (25° C.) for 2 hours to conduct an acid hydrolysis reaction. After that, this reaction solution was concentrated under a reduced pressure to yield 202.8 mg of a yellow amorphous compound (1"a-2) as a mixture with sodium chloride.

Compound (1"a-2)

$^1$H NMR (500 MHz, $D_2O$): δ 4.32 (dd, J=9.8, 7.0 Hz, 1H), 4.06 (dd, J=7.0, 4.7 Hz, 1H), 3.86 (ddd, J=11.4, 7.9, 3.8 Hz, 1H), 3.73 (t, J=6.0 Hz, 2H), 3.64 (ddd, J=13.0, 9.8, 6.6 Hz, 1H), 3.45 (ddd, J=13.0, 9.8, 5.7 Hz, 1H), 3.26 (m, 1H), 3.25 (t, J=7.6 Hz, 2H), 2.57 (m, 1H), 3.46-2.33 (m, 2H), 2.28-2.18 (n, 2H), 2.04 (m, 1H), 1.97 (quintet, J=6.3 Hz, 2H).

Example 2

Indicated are a production example of a compound (1"b) in which $R^1$ and $R^2$ are ethyl groups, $R^3$ is a hydroxyl group, and n is 1 in the general formula (1), and a production example of a compound (1"b-2) which is a salt of a compound in which $R^1$ and $R^2$ are hydrogen atoms, $R^3$ is a hydroxyl group, and n is 1 in the general formula (1) (hereinafter, referred to also as "derivative (X')").

(1) Step 1

A methanol solution of 401.2 mg (1.87 mmol) of Boc-D-allylglycine (5b) was cooled to −78° C., and ozone gas was used and bubbled until the solution turned blue. Then, nitrogen gas was bubbled until the blue color disappeared, and 430 mg (3.73 mmol) of L-proline (6a) and 235 mg (3.74 mmol) of sodium cyanoborohydride (NaBH$_3$CN) were added to this reaction solution. The materials were stirred at room temperature (25° C.) for 2 hours to conduct a reaction. The completion of the reaction was confirmed by TLC, and the reaction solution was concentrated under a reduced pressure. Subsequently, the obtained residue was purified by flash column chromatography to yield 689.3 mg of a white oily compound (4b). The developing solvent for flash column chromatography is ethyl acetate:methanol=1:1 to 0:1.

(2) Step 2

To 689.3 mg of the compound (4b), cooled anhydrous HCl/EtOH (HCl/EtOH prepared using 1.8 mL of acetyl chloride and 9 mL of ethanol) was added, and the materials were stirred at 50° C. for 17 hours to deprotect an amino-protecting group while protecting a carboxyl group. The completion of the reaction was confirmed by TLC, and the reaction solution was concentrated under a reduced pressure. Subsequently, the obtained residue was washed with diethyl ether, and a 0.1M aqueous sodium hydroxide solution was added to the collected aqueous layer. Dichloromethane was added to this mixed solution for extraction, and the collected organic layer was dried over magnesium sulfate. After that, filtration was performed, and the filtrate was concentrated under a reduced pressure to yield 525.3 mg of a colorless oily compound (3b).

(3) Step 3

To 18 mL of a methanol solution of 525.3 mg (1.93 mmol) of the compound (3b), 435 mg (2.31 mmol) of an aldehyde compound (2a) was added, and the materials were cooled to 0° C. To this mixed solution, 5.5 mL (96.1 mmol) of acetic acid and 135 mg (2.15 mmol) of NaBH$_3$CN were added. The mixture was stirred at 0° C. for 16 hours to react the compound (3b) with the aldehyde compound (2a). Subsequently, the completion of the reaction was confirmed by TLC, and a saturated aqueous sodium hydrogen carbonate solution was added to this reaction solution. Dichloromethane was added to this reaction solution for extraction, and the collected organic layer was dried over magnesium sulfate. After that, filtration was performed and the filtrate was concentrated under a reduced pressure. The obtained residue was purified by flash column chromatography to yield 372.6 mg (0.84 mmol, 44%) of a colorless oily compound (1'b). The developing solvent for flash column chromatography is n-hexane:ethyl acetate=1:1 to 0:1.

Compound (1'b)

$^1$H NMR (400 MHz, CD$_3$OD): δ 4.16 (q, J=7.3 Hz, 2H), 4.15 (q, J=7.3 Hz, 2H), 3.69 (t, J=5.7 Hz, 2H), 3.36-3.30 (m, 1H), 3.20-3.10 (m, 2H), 2.81 (dt, J=12.0, 7.8 Hz, 1H), 2.66 (dt, J=11.3, 7.0 Hz, 1H), 2.58 (dt, J=11.3, 7.0 Hz, 1H), 2.46 (ddd, J=13.0, 7.5, 5.5 Hz, 1H), 2.32 (m, 1H), 2.12 (m, 1H), 1.91-1.78 (m, 5H), 1.70 (quintet, J=6.3 Hz, 2H), 1.26 (t, J=7.3 Hz, 3H), 1.25 (t, J=7.3 Hz, 3H), 0.89 (s, 9H), 0.05 (s, 6H).

(4) Step 4

To 372.6 mg (0.84 mmol) of the compound (1'b), 2.4 mL of acetic acid, 0.8 mL of THF and 0.8 mL of water were added, and the materials were stirred at room temperature (25° C.) for 17 hours. Then, the temperature of the mixed solution was raised to 40° C., and the mixed solution was stirred additionally for 2 hours to conduct a deprotecting reaction. The completion of the reaction was confirmed by TLC, and the reaction solution was concentrated under a reduced pressure. Subsequently, the obtained residue was dissolved in ethyl acetate, and a saturated aqueous sodium hydrogen carbonate solution was added. Dichloromethane was then added to this mixed solution for extraction, and the collected organic layer was dried over magnesium sulfate. After that, filtration was performed and the filtrate was concentrated under a reduced pressure. The obtained residue was purified by flash column chromatography to yield 111.6 mg (0.34 mmol, 40%) of a colorless oily compound (1"b). The developing solvent for flash column chromatography is ethyl acetate:methanol=5:1.

Compound (1"b)

$^1$H NMR (400 MHz, CD$_3$OD): δ 4.18 (q, J=7.0 Hz, 2H), 4.17 (q, J=7.0 Hz, 2H), 3.61 (t, J=6.2 Hz, 2H), 3.34 (t, J=6.3 Hz, 1H), 3.20-3.11 (m, 2H), 2.82 (dt, J=12.0, 7.8 Hz, 1H), 2.68 (dt, J=11.3, 7.0 Hz, 1H), 2.60 (dt, J=11.3, 7.0 Hz, 1H), 2.47 (m, 1H), 2.32 (qd, J=8.3, 2.8 Hz, 1H), 2.11 (m, 1H), 1.89-1.78 (m, 5H), 1.70 (quintet, J=6.8 Hz, 2H), 1.26 (t, J=7.0 Hz, 3H), 1.25 (t, J=7.0 Hz, 3H).

(5) Step 5

The compound (1"b) was dissolved in water, and then the aqueous solution was cooled to 0° C. Subsequently, a 1M aqueous sodium hydroxide solution was added to this aqueous solution, the temperature was raised to room temperature (25° C.), and the mixture was stirred to conduct a deprotecting reaction. The reaction solution was concentrated under a reduced pressure. A 1M aqueous hydrogen chloride solution was added to the obtained residue, and the mixture was stirred at room temperature (25° C.) for 2 hours to conduct an acid hydrolysis reaction. After that, the reaction solution was concentrated under a reduced pressure to yield a yellow amorphous compound (1"b-2).

Compound (1″b-2)

$^1$H NMR (500 MHz, D$_2$O): δ 4.38 (dd, J=9.8, 7.3 Hz, 1H), 4.12 (dd, J=7.9, 5.7 Hz, 1H), 3.86 (ddd, J=11.1, 7.6, 3.8 Hz, 1H), 3.72 (t, J=6.0 Hz, 2H), 3.62 (ddd, J=12.6, 9.5, 6.0 Hz, 1H), 3.61 (m, 1H), 3.28 (m, 1H), 3.25 (t, J=7.6 Hz, 2H), 2.59 (m, 1H), 2.50-2.38 (m, 2H), 2.28-2.18 (m, 2H), 2.07 (m, 1H), 1.97 (quintet, J=6.6 Hz, 2H).

Example 3

Indicated are a production example of a compound(1‴a) in which R$^1$ and R$^2$ are ethyl groups, R$^3$ is a tert-butyl group, and n is 1 in the general formula (1), and a production example of a compound (1‴a-2) which is a salt of a compound in which R$^1$ and R$^2$ are hydrogen atoms, R$^3$ is a carboxyl group, and n is 1 in the general formula (1) (hereinafter, referred to also as "derivative (Y)"), using the compound (3a) obtained in Example 1 as a raw material.

(1) Step 3'

To 7.7 mL of a methanol solution of 209.3 mg (0.77 mmol) of the compound (3a), 150 mg (0.95 mmol) of an aldehyde compound (2c) was added, and the materials were cooled to 0° C. To this mixed solution, 2.2 mL (38.4 mmol) of acetic acid and 53 mg (0.84 mmol) of NaBH$_3$CN were added. The mixture was stirred at 0° C. for 14 hours to react the compound (3a) with the aldehyde compound (2c). Subsequently, the completion of the reaction was confirmed by TLC, and a saturated aqueous sodium hydrogen carbonate solution was added to this reaction solution. Ethyl acetate was added to this mixed solution for extraction, and the collected organic layer was dried over magnesium sulfate. After that, filtration was performed and the filtrate was concentrated under a reduced pressure. The obtained residue was purified by flash column chromatography to yield 143.7 mg (0.35 mmol) of a colorless oily compound (1‴a). The developing solvent for flash column chromatography is n-hexane:ethyl acetate=2:1 to 0:1.

Compound (1‴a)

$^1$H NMR (400 MHz, CD$_3$OD): δ 4.17 (q, J=7.3 Hz, 2H), 4.16 (q, J=7.3 Hz, 2H), 3.34-3.32 (m, 1H), 3.14 (m, 1H), 2.79 (ddd, J=12.0, 8.6, 7.3 Hz, 1H), 2.58 (dt, J=11.8, 7.6 Hz, 1H), 2.45 (m, 1H), 2.34 (br q, J=8.3 Hz, 1H), 2.26 (t, J=7.3 Hz, 2H), 2.10 (m, 1H), 1.92-1.66 (m, 7H), 1.49 (s, 9H), 1.26 (t, J=7.0 Hz, 3H), 1.25 (t, J=7.0 Hz, 3H).

(2) Step 4'

96.1 mg (0.23 mmol) of the compound (1‴a) was dissolved in water, and then 2.3 mL of the aqueous solution was cooled to 0° C. Subsequently, 0.5 mL of a 1M aqueous sodium hydroxide solution was added to this aqueous solution. The temperature was raised to room temperature (25° C.), and the mixture was stirred for 19 hours to conduct a deprotecting reaction. The completion of the reaction was confirmed by TLC, and the reaction solution was concentrated under a reduced pressure. To the obtained residue, 2.3 mL of a 1M aqueous hydrogen chloride solution was added, and the mixture was stirred at room temperature (25° C.) for 2 hours to conduct an acid hydrolysis reaction. After that, this reaction solution was concentrated under a reduced pressure to yield 133.7 mg of a yellow amorphous compound (1‴a-2) as a mixture with sodium chloride.

Compound (1‴a-2)

$^1$H NMR (500 MHz, D$_2$O): δ 4.33 (dd, J=9.5, 7.0 Hz, 1H), 4.07 (dd, J=8.5, 4.5 Hz, 1H), 3.86 (ddd, J=11.4, 7.9, 4.1 Hz, 1H), 3.64 (ddd, J=12.9, 9.8, 6.3 Hz, 1H), 3.45 (ddd, J=12.9, 9.8, 5.6 Hz, 1H), 3.29 (m, 1H), 3.20 (t, J=7.8 Hz, 2H), 2.57 (m, 1H), 2.56 (t, J=7.0 Hz, 2H), 2.47-2.34 (m, 2H), 2.27-2.18 (m, 2H), 2.11-1.98 (m, 3H).

(Evaluation)

The derivatives (X), (X') and (Y) obtained above were evaluated as follows.

(1) Stability Test in Acidic Aqueous Solution

In this stability test, whether acidic aqueous solutions prepared using the derivatives (X), (X') and (Y), and 2'-deoxymugineic acid (DMA) and a compound having the following structure (hereinafter, referred to as "PDMA") were stable along with the lapse of time, i.e., whether the derivatives were difficult to decompose was evaluated.

Test Examples 1 to 3 and Referential Examples 1 and 2

The following test solutions (a), (b) and (c) were prepared using the derivatives (X), (X') and (Y). Also, the following test solutions (d) and (e) were prepared using DMA and PDMA. The test solution (a) was prepared by dissolving 3 μmol of the substance in 0.5 mL of heavy water. Other test solutions were prepared by dissolving 0.03 mmol of the substance in 0.5 mL of heavy water. The pH of the test solution was 2.

Test solution (a) for Test Example 1: acidic aqueous solution of the derivative (X)
Test solution (b) for Test Example 2: acidic aqueous solution of the derivative (X')
Test solution (c) for Test Example 3: acidic aqueous solution of the derivative (Y)
Test solution (d) for Referential Example 1: acidic aqueous solution of DMA
Test solution (e) for Referential Example 2: acidic aqueous solution of PDMA An NMR measuring tube (manufactured by Kanto Chemical Co., Inc., φ5 mm×7 inch) was filled with each of the test solutions (a) to (e), and $^1$H NMR measurement was performed. $^1$H NMR was measured immediately after (0 day), 10 days after, 20 days after, and 27 days after the preparation of the test solution. The test solutions were stored at room temperature (25° C.) in a sealed state in which they were placed in the NMR measuring tubes, while being protected from light.

Figure 1:
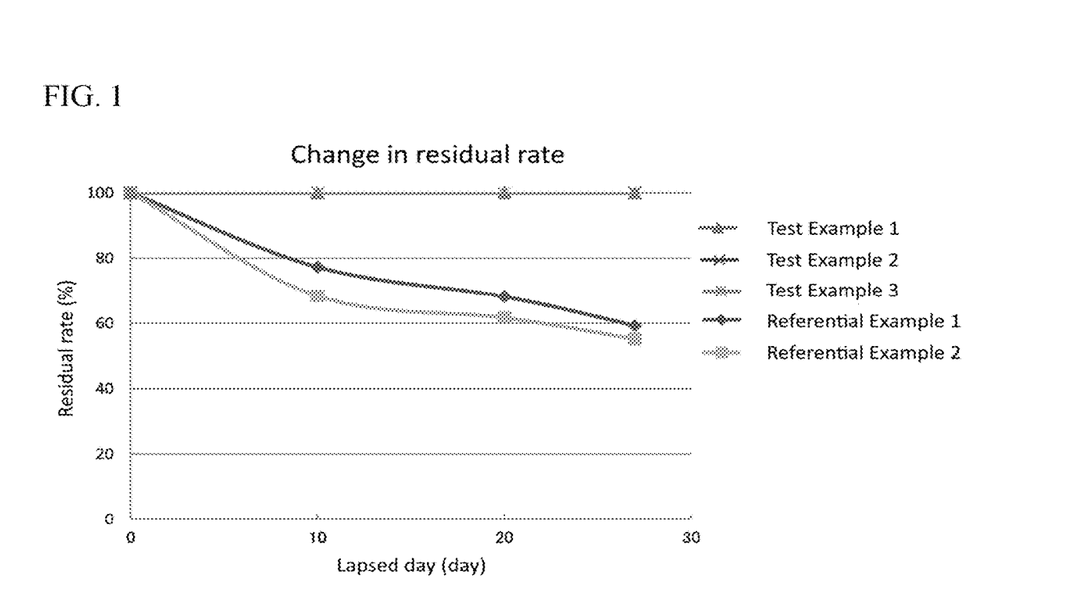
FIG. 1 is a graph showing results of Test Examples and Referential Examples in a stability test in an acidic aqueous solution.

Attention was paid to 4.4 ppm (1H, q) for DMA, 4.4 ppm (1H, q) for PDMA, 4.3 ppm (1H, dd) for the derivative (X), 4.3 ppm (1H, dd) for the derivative (X'), and 4.3 ppm (1H, dd) for the derivative (Y) in the resulting $^1$H NMR spectrum. In the case of the test solutions (a), (b) and (c), no change was observed in the $^1$H NMR spectrum even when the storage period was 27 days. On the other hand, in the case of the test solutions (d) and (e), peaks derived from decomposition products of DMA and PDMA were detected with the lapse of the storage time. The chemical shifts of the peaks were 4.5 ppm (t, 1H) for DMA and 4.5 ppm (1H, t) for PDMA. Thus, from the integrated values, the residual rate of DMA or PDMA after 10, 20, and 27 days was calculated based on the following calculation formula (see Table 1 and FIG. 1):

(Integrated value of measured compound)/{(integrated value of measured compound)+(integrated value of decomposition product)}×100

TABLE 1

(Change of residual rate)

|  | Test solution | pH | Lapsed day (day) | | | |
|---|---|---|---|---|---|---|
|  |  |  | 0 | 10 | 20 | 27 |
| Test Example 1 | (a) (Derivative (X)) | 2.0 | 100% | 100% | 100% | 100% |
| Test Example 2 | (b) (Derivative (X')) | 2.0 | 100% | 100% | 100% | 100% |
| Test Example 3 | (c) (Derivative (Y)) | 2.0 | 100% | 100% | 100% | 100% |
| Referential Example 1 | (d) (DMA) | 2.0 | 100% | 77.3% | 68.2% | 59.3% |
| Referential Example 2 | (e) (PDMA) | 2.0 | 100% | 68.4% | 61.7% | 55.2% |

As shown in Table 1 and FIG. 1, in Test Examples 1 to 3 relating to the derivative (X), the derivative (X') and the derivative (Y), no peak derived from the decomposition product was detected after a lapse of 27 days from the beginning of the preparation of each of the test solutions, and the residual rate was always maintained at 100%, indicating extremely high stability. On the other hand, in Referential Examples 1 and 2, the residual rates of DMA and PDMA significantly decreased by the $10^{th}$ day and continued to decrease thereafter. It was found that DMA and PDMA were inferior, in stability in an acidic aqueous solution, to the derivative (X), the derivative (X') and the derivative (Y) according to the present invention.

(2) Cultivation Test

Test Examples 4 to 6 and Referential Examples 3 and 4

The paddy rice variety "Nipponbare" was seeded in tap water. When roots and buds emerged, seedlings were soaked in a hydroponic solution (formulation in the Horticultural Experiment Station). When the height of the plant reached about 5 cm, the seedlings were transplanted to shell fossil soil of pH 9. Then, the following fertilizers (f) to (h) were prepared for Test Examples 4 to 6, and the following fertilizer (i) was prepared for Referential Example 3.

Figure 2:
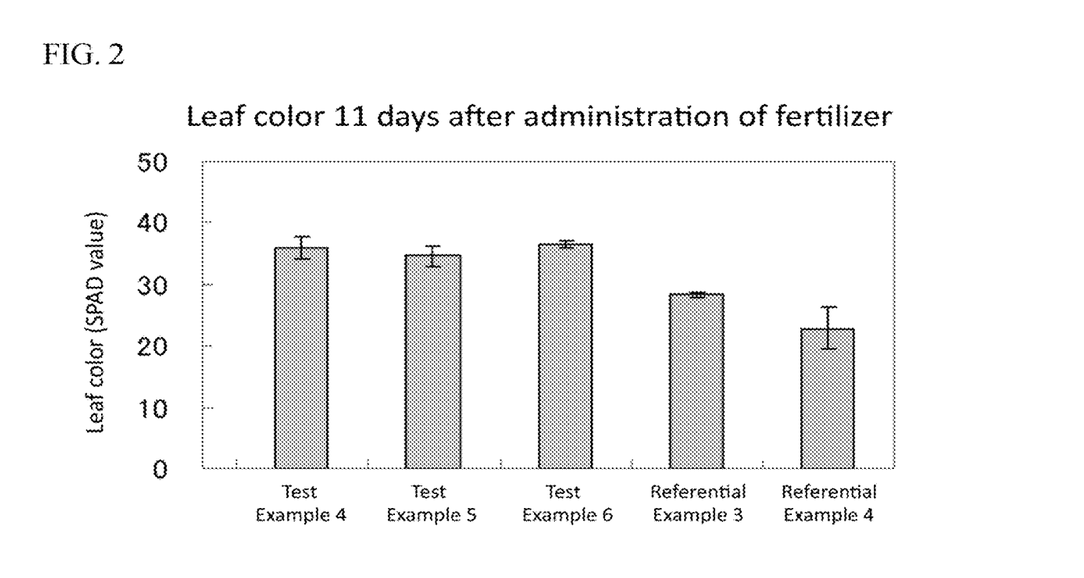
FIG. 2 is a graph showing results of Test Examples and Referential Examples in a cultivation test.

Subsequently, the fertilizers (f) to (i) were administered to each separate seedling only once (dose of the derivative: 90 μmol), and then soil was irrigated three times a week until the soil reached a saturated water capacity. The leaf color (SPAD value) of rice was measured 11 days after the administration of each of the fertilizers. In addition, Referential Example 4 is an example in which cultivation was performed only by irrigation without application of a fertilizer, and the SPAD value was measured on the 11th day as in Test Example 4 and the like. The results are shown in FIG. 2.

Fertilizer (f) for Test Example 4: 1:1 mixture of the derivative (X) and iron sulfate Fertilizer (g) for Test Example 5: 1:1 mixture of the derivative (X') and iron sulfate Fertilizer (h) for Test Example 6: 1:1 mixture of the derivative (Y) and iron sulfate Fertilizer (i) for Referential Example 3: Fe-EDDHA Referential Example 4: no fertilizer As shown in FIG. 2, the SPAD value on the 11th day was 33 to 38 in all of Test Examples 4 to 6 using the fertilizer containing the derivative (X), (X') or (Y) according to the present invention, and it was seen that the fertilizer has a high growth effect. On the other hand, the SPAD value was 28 to 29 in Referential Example 3 using the fertilizer consisting of Fe-EDDHA (iron-ethylenediamine-N,N'-bis(2-hydroxyphenylacetic acid)) as a general synthetic chelate iron complex, and was 19 to 26 in Referential Example 4 without a fertilizer. Thus, it was revealed that, when the fertilizers according to the present invention were used, rice developed an intense leaf color and grew satisfactorily, as compared with not only the case where no fertilizer was applied, but also the case where a general synthetic chelate iron complex was used.

From the results above, it was found that the heterocycle-containing amino acid compound or salt thereof of the present invention has both an excellent action as an iron chelating agent and stability in an acidic aqueous solution such that it is difficult to decompose with the lapse of time.

[Industrial Applicability]

The heterocycle-containing amino acid compound or salt thereof of the present invention can be utilized in uses and technical fields of a fertilizer, a plant growth regulating agent, and the like.

The invention claimed is:

1. A heterocycle-containing amino acid compound represented by a general formula (1):

wherein $R^1$ and $R^2$ are identical with or different from each other, and each represent a hydrogen atom or a carboxy-protecting group;

$R^3$ represents a carboxyl group or a hydroxyl group; and n is 1 or 2, or a salt thereof.

2. The heterocycle-containing amino acid compound or salt thereof according to claim 1, wherein the heterocycle-containing amino acid compound represented by the general formula (1) is a compound represented by a general formula (1A):

(1A)

wherein $R^1$, $R^2$, $R^3$ and n are respectively the same as those in the general formula (1).

3. The heterocycle-containing amino acid compound or salt thereof according to claim 1,
wherein the heterocycle-containing amino acid compound represented by the general formula (1) is a compound represented by a general formula (1B):

(1B)

wherein $R^1$, $R^2$, $R^3$ and n are respectively the same as those in the general formula (1).

4. The heterocycle-containing amino acid compound or salt thereof according to claim 1,
wherein $R^1$ and $R^2$ in the general formula (1) are hydrogen atoms.

5. The heterocycle-containing amino acid compound or salt thereof according to claim 1
wherein n in the general formula (1) is 1.

6. A complex comprising the heterocycle-containing amino acid compound or salt thereof according to claim 1 and a metal.

7. The complex according to claim 6, wherein the metal is an iron.

8. A composition comprising the heterocycle-containing amino acid compound or salt thereof according to claim 1 and a metal compound.

9. The composition according to claim 8, wherein the metal compound is an iron compound.

10. The composition according to claim 8, which is used for a fertilizer or a plant growth regulating agent.

11. A fertilizer comprising the heterocycle-containing amino acid compound or salt thereof according to claim 1.

12. A plant growth regulating agent comprising the heterocycle-containing amino acid compound or salt thereof according to claim 1.

* * * * *